US008614178B2

(12) United States Patent
Theisinger et al.

(10) Patent No.: US 8,614,178 B2
(45) Date of Patent: Dec. 24, 2013

(54) PHARMACEUTICAL COMPOSITION FOR TREATMENT OF DRY EYE SYNDROME

(75) Inventors: Bastian Theisinger, Mannheim (DE); Sonja Theisinger, Mannheim (DE); Bernhard Günther, Dossenheim (DE)

(73) Assignee: Novaliq GmbH, Heidelberg (DE)

( * ) Notice: Subject to any disclaimer, the term of this patent is extended or adjusted under 35 U.S.C. 154(b) by 0 days.

(21) Appl. No.: 13/513,886

(22) PCT Filed: Dec. 13, 2010

(86) PCT No.: PCT/EP2010/069495
§ 371 (c)(1),
(2), (4) Date: Jun. 5, 2012

(87) PCT Pub. No.: WO2011/073134
PCT Pub. Date: Jun. 23, 2011

(65) Prior Publication Data
US 2012/0244177 A1    Sep. 27, 2012

(30) Foreign Application Priority Data

Dec. 14, 2009 (EP) ..................................... 09015423

(51) Int. Cl.
*A61K 38/00*    (2006.01)
(52) U.S. Cl.
USPC ........................................................ 514/1.1
(58) Field of Classification Search
None
See application file for complete search history.

(56) References Cited

U.S. PATENT DOCUMENTS

| 6,262,126 | B1 | 7/2001 | Meinert |
| 6,372,243 | B2 | 4/2002 | Kobuch et al. |
| 7,001,607 | B1 | 2/2006 | Menz et al. |
| 2003/0018044 | A1* | 1/2003 | Peyman ........................ 514/291 |

FOREIGN PATENT DOCUMENTS

| WO | 96/40052 A1 | 12/1996 |
| WO | 2005/099718 A1 | 10/2005 |
| WO | 2005/123035 A1 | 12/2005 |
| WO | WO 2005123035 A1 * | 12/2005 |

OTHER PUBLICATIONS

Mackiewicz et al., Investigative Ophthalmology & Visual Science, Apr. 2007, vol. 48, No. 4, 1873-1883.*
Meinert H. et al: "Semifluorinated alkanes—a new class of compounds with outstanding properties for use in ophthalmology". European Journal of Ophthalmology, Milan, IT, vol. 10, No. 3, Jul. 1, 2000, pp. 189-197, XP009134460, ISSN: 1120-6721 abstract.
Allergan, Inc.: "Restasis(R)"—Informational Sheet. (C) 2009 Allergan, Inc.
Gayton, Johnny L.: "Etiology, prevalence, and treatment of dry eye disease". Clinical Ophthalmology 2009:3, pp. 405-412; Jul. 3, 2009, Dove Medical Press, Ltd.
Lemp, Michael A., MD; "Management of Dry Eye Disease". The American Journal of Managed Care, 2008; vol. 14, No. 3 pp. S88-S101.
Perry, Henry D., MD; "Dry Eye Disease: Pathophysiology, Classification and Diagnosis".The American Journal of Managed Care, 2008; vol. 14, No. 3 pp. S79-S87.
Meinert, H. et al.: "The Use of Semifluorinated Alkanes in Blood-SUbstitutes". Biomat., Art. Cells & Immob Biotech., 21(5), 583-595 (1993).

* cited by examiner

*Primary Examiner* — Marcela Cordero Garcia
*Assistant Examiner* — Kaipeen Yang
(74) *Attorney, Agent, or Firm* — Dennemeyer & Associates, LLC.

(57) ABSTRACT

The invention provides novel pharmaceutical compositions for the treatment of keratoconjunctivitis sicca comprising liquid vehicles which include one or more semifluorinated alkanes. The compositions incorporate an active ingredient selected from the group of macrolide immunosuppressants. They can be administered topically into the eye. The invention further provides kits comprising such compositions.

13 Claims, No Drawings

PHARMACEUTICAL COMPOSITION FOR TREATMENT OF DRY EYE SYNDROME

BACKGROUND

Keratoconjunctivitis sicca, also known as dry eye disease or dysfunctional tear syndrome, is today understood as a multifunctional disorder of the tear film and of the ocular surface which results in discomfort, visual disturbance, and often even in ocular surface damage caused by tear film instability. Its prevalence differs widely by regions and is estimated to range from about 7.4% in the USA to about 33% in Japan (J. L. Gayton, Clinical Ophthalmology 2009:3, 405-412). According to another estimate, approximately 3.2 million women and 1.05 million men suffer from keratoconjunctivitis sicca in the USA alone. If symptomatically mild cases are also considered, there could be as many as 20 million affected people in the USA.

The main physiological function of the tear film is the lubrication of the ocular surface and the inner eyelid. In addition, it supplies the ocular surface with the nutrients which it requires, provides a smooth and regular optical surface for the eye. Moreover, it protects the ocular surface against pathogens by various mechanisms, including mechanical removal of foreign particles but also through antimicrobial substances which it contains.

The tear film is composed of a mucous component, an aqueous component, and a lipid component. The inner layer of the film is the mucous layer or component, which is bound to the ocular epithelium via the interaction of mucin molecules which are produced by conjunctival goblet cells and by stratified squameous cells of the conjunctiva and the cornea. The lubricating effect of the tear film is substantially based on the mucous layer and its composition.

On top of the mucous layer is the aqueous layer which is produced by the main and accessory lacrimal glands. Its primary function is to hydrate the mucous component and contribute to the transport of nutrients, electrolytes, antibacterial compounds, and oxygen to the ocular surface. The aqueous component contains water, electrolytes, lysozyme, lactoferrin, immunoglobulins in particular IgA), retinol, hepatocyte growth factor, epidermal growth factor as its important constituents.

The lipid layer which covers the aqueous layer is produced by the tarsal glands which are positioned at the tarsal plates of the eyelids, and to some degree also by the glands of Zeis which open into the eyelash follicles. Its functions include the enhancement of the spreading of the tear film, decrease of water loss from the aqueous layer by reducing evaporation, and preventing tear film contamination.

It is today acknowledged that keratoconjunctivitis sicca is a complex, multifunctional disorders involving several interacting pathophysiological mechanisms which are only beginning to be understood (H. D. Perry, Am. J. Man. Care 13:3, S79-S87, 2008). The two mechanisms that are being discussed as pivotal in the etiology of the disease and which also appear to reinforce each other mutually are tear hyperosmolarity and tear film instability. Hyperosmolar tear fluid can result from excessive tear film evaporation or reduced aqueous flow. It activates an inflammatory cascade and causes the release of inflammatory mediators into the tear fluid, with multiple pathophysiological effects eventually leading to increased tear film evaporation and tear film instability. Thus, tear film instability can be a consequence of hyperosmolarity. Alternatively, it can develop as the original etiological pathway, e.g. via abnormalities of the lipid layer composition, such as in tarsal gland disease).

Once keratoconjunctivitis sicca has become manifest, inflammation is one of the key processes that maintain and potentially progress the disease. Depending on the severity of the condition, patients often develop a reversible squameous metaphase and punctate erosions of the ocular epithelium. Secondary diseases whose development may be triggered by keratoconjunctivitis sicca include filamentary keratitis, microbial keratitis, corneal neovascularisation, and ocular surface keratinisation.

Two major categories of keratoconjunctivitis sicca or dry eye disease (DED) are distinguished today, which are aqueous-deficient DED and evaporative DED. Within the class of aqueous-deficient forms of DED, two major subtypes are differentiated, Sjögren and non-Sjögren. Sjögren syndrome patients suffer from autoimmune disorders in which the lacrimal glands are invaded by activated T-cells, which leads not only to keratoconjunctivitis sicca but also to a dry mouth condition. The Sjögren syndrome can be a primary disease or result from other autoimmune diseases such as systemic lupus erythrematosus or rheumathroid arthritis. Non-Sjögren patients suffering from an aqueous-deficient DED usually have a lacrimal gland insufficiency, lacrimal duct obstruction or reflex hyposecretion. The second major class, evaporative DED, is also somewhat heterogeneous and can develop as a result of diverse root causes. One of the major causes is meibomian gland disease, eyelid aperture disorders, blink disorders (as in Parkinson disease) or ocular surface disorders (as in allergic conjunctivitis).

Among the many risk factors for keratoconjunctivitis sicca that are known today, some of the best studied ones are advanced age and female sex. It appears that in particular postmenopausal women have a reduced tear production, probably related to hormonal effects which are not very well understood as yet. Further risk factors include diets with low omega-3-fatty acids, occupational factors (e.g. associated with reduced blink frequency), environmental conditions, contact lens wearing, certain systemic (anticholinergics, beta-blockers, isotretinoin, interferons, hormones) and ophthalmic medications (any frequently administered eye drops including artificial tears; especially formulations comprising preservatives), and a number of primary diseases such as Parkinson disease, hepatitis C, HIV infection, and diabetes mellitus.

The management of keratoconjunctivitis sicca relies on both non-pharmacological and pharmacological approaches and the therapeutic options depend significantly on the severity of the disease state (M. A. Lemp, Am. J. Man. Care 14:3, S88-S101, 2008). Non-pharmacological approaches may be used initially when only mild symptoms occur, or as palliative measures to support medical interventions. They include the avoidance of exacerbating factors such as dry air, wind and drafts, tobacco smoke, modification of working habits; eye lid hygiene; tear supplementation, and physical tear retention by punctal plugs or therapeutic contact lenses.

The mainstay of non-pharmacological DED treatment is the use of artificial tears for tear substitution. Most of the available products are designed as lubricants. In addition, they may function as carriers for nutrients and electrolytes (importantly, potassium and bicarbonate), and some products attempt to correct physical parameters such as an increased osmolarity in certain forms of DED. The major functional component of artificial tear compositions is an agent which increases or adjusts the viscosity and which at the same time exhibits lubricant functionality. Common compounds used for this purpose include carboxymethylcellulose and its sodium salt CCMC, carmellose), polyvinyl alcohol, hydroxypropyl methylcellulose (HPMC, hypromellose), hyaluronic acid and its sodium salt, and hydroxypropyl guar gum. However, compositions with a relatively high viscosity, and in particular gel-type formulations, have a tendency to cause visual blurring.

Some artificial tears comprise lipids to substitute for the lipid component of the natural tear film. Unfortunately, the commonly used lipids are physically and biochemically poorly related to native lipid compositions: they are based on castor oil or even mineral oil. It is intended to thereby decrease the rate of tear fluid evaporation. The same effect may perhaps also be achieved by hydrocolloids which exhibit some degree of bioadhesiveness, such as hydroxypropyl guar gum or hyaluronic acid.

At least in earlier years, multi-dose formulations for ophthalmic administration had to be preserved using a physiologically acceptable preservative in order to reduce the risk of microbial contamination and infection. Most preservatives are however problematic for DED patients in that they have a potential to negatively affect the ocular surface, thus counteracting the therapeutic intent. As an alternative, single-dose containers for the administration of non-preserved formulations were developed. These are however less convenient to handle than the conventional multi-dose bottles.

For moderate to severe forms of keratoconjunctivitis sicca, non-pharmacological approaches are not normally sufficient to manage the symptoms adequately. However, there are presently not many pharmacological therapies available which have proven to be effective and/or which have been authorised by the regulatory agencies.

Cholinergic agents such as muscarinic acetylcholine receptor antagonists may be used in aqueous deficient patient as secretagogues to stimulate tear production. An agent that has been tested successfully in several clinical studies with Sjögren syndrome patients is pilocarpine. The drug given orally at doses of 5 to 7.5 mg QID (Lemp, ditto) significantly improved DED symptoms. However, the product has not been approved by any major regulatory agencies for the use in keratoconjunctivitis sicca, neither as an oral formulation nor in the form of eye drops as they are available for the treatment of glaucoma.

Cevimeline is another parasympathomimetic drug and muscarinic agonist. It acts particularly on muscarinic M3 receptors. It is available in a few countries as an oral formulation and used in the treatment of dry mouth associated with Sjögren's syndrome. Clinical studies indicate that it is also effective in the management of symptoms associated with keratoconjunctivitis sicca of the Sjögren type, for which it is being used off-label like pilocarpine.

Anti-inflammatory agents may be used to intervene in the viscous circle of symptoms causing inflammatory response which in turn increase symptom severity. The rationale of using such agents is not restricted to aqueous deficient or even Sjögren syndrome patients. Both topical corticosteroids and topical non-steroidal anti-inflammatory (NSAID) compounds have been proposed as treatment options.

From the clinical studies that have been conducted so far (Lemp, ditto.) it appears that corticosteroids such as loteprednol etabonate and prednisolone acetate are more effective in the control of several DED symptoms than NSAIDs such as diclofenac and ketorolac. However, they are generally recommended only for short-term use. In the long term, they may cause or support the development of ocular infections, glaucoma, and cataracts. Both loteprednol etabonate and prednisolone acetate are poorly water-soluble and thus formulated as a suspension, which may be considered a disadvantage in view of the symptoms of keratoconjunctivitis sicca.

Moreover, clinical studies with, and the off-label use of, oral tetracyclines such as doxycyclin, minocycline and oxytetracycline for keratoconjunctivitis sicca have been reported (Lemp, ditto.). It is assumed that they are not primarily effective on the basis of their antibacterial properties, but due to their anti-inflammatory activity.

At least in the USA, the major pharmacological treatment option for moderate to severe keratoconjunctivitis sicca is ciclosporin (i.e. ciclosporin A, also known as cyclosporine A), which is an approved medicine in the form of an ophthalmic emulsion (Restasis®) for increasing " . . . tear production in patients whose tear production is presumed to be suppressed due to ocular inflammation associated with keratoconjunctivitis sicca." (Restasis prescribing information). According to the evidence that is available, topical ciclosporin is probably disease-modifying rather than only palliative. It acts as an antagonist in various inflammatory processes and cascades. For example, it reduces conjunctival interleukin-6 (IL-6) levels, decreases activated lymphocytes in the conjunctiva, suppresses other conjunctival inflammatory and apoptotic markers, and increases the number of goblet cells in the conjunctiva (Lemp, ditto.).

Ciclosporin (IUPAC name: (E)-14,17,26,32-tetrabutyl-5-ethyl-8-(1-hydroxy-2-methylhex-4-enyl)-1,3,9,12,15,18,20, 23,27-nonamethyl-11,29-dipropyl-1,3,6,9,12,15,18,21,24, 27,30-undecaazacyclodotriacontan-2,4,7,10,13,16,19,22,25, 28,31-undecaone; $C_{62}H_{111}N_{11}O_{12}$; MW1202.61) is a cyclic nonribosomal peptide of 11 amino acids, originally discovered as a product of the fungus *Beauveria nivea*. It is an immunosuppressant drug widely used in post-allergenic organ transplant to reduce the activity of the patient's immune system and, so, the risk of organ rejection.

Ciclosporin is thought to bind to the cytosolic protein cyclophilin (immunophilin) of immunocompetent lymphocytes, especially T-lymphocytes. This complex of ciclosporin and cyclophilin inhibits calcineurin, which, under normal circumstances, is responsible for activating the transcription of interleukin 2. It also inhibits lymphokine production and interleukin release and, therefore, leads to a reduced function of effector T-cells.

Other immunosuppressant drugs with similar activity include tacrolimus, pimecrolimus, everolimus, sirolimus, deforolimus, temsirolimus, and zotarolimus, abetimus, gusperimus, and mycophenolic acid. Based on pharmacological considerations, it is presumed that these compounds would also be beneficial in the management of diseases or symptoms which are controlled by ciclosporin, such as dry eye disease or keratoconjunctivitis sicca.

Macrolide immunosuppressants such as ciclosporin, tacrolimus, sirolimus, everolimus and the like, while being highly active once they have been effectively delivered into the organism or to the target tissue, are challenging compounds to formulate and deliver to the site of action, in particular due to their extremely poor solubility and relatively large molecular size. For systemic therapy via the oral or intravenous routes of administration, they are typically presented as solubilised formulations comprising substantial amounts of solubilising excipients, such as surfactants and organic solvents.

The ophthalmic product, Restasis, which comprises ciclosporin at a concentration of 0.05%, is formulated as a sterile, preservative-free oil-in-water (o/w) emulsion. The formulation is white opaque to slightly translucent presented in single-use LDPE vials filled with 0.4 mL liquid. As inactive ingredients, it contains glycerine, castor oil, polysorbate 80, carbomer 1342, purified water and sodium hydroxide to adjust the pH to 6.5 to 8.0. The active ingredient is dissolved in the dispersed oily phase of the emulsion consisting of castor oil. It is assumed that the amphiphilic polysorbate 80 and probably also the carbomer act as stabilisers of the emulsion. The major adverse effects of Restasis include ocular burning and stinging, occurring in a phase III trial at a frequency of 14.7% and 3.4%, respectively. Other events reported in 1 to 5% of the patients include conjunctival hyperaemia, discharge, epiphora, eye pain, foreign body sensation, pruritus, and visual disturbance which is typically blurring (Restasis Prescribing Information).

Other ophthalmic formulations of ciclosporin are known from U.S. Pat. No. 5,411,952 and U.S. Pat. No. 4,839,342.

The latter discloses a 2% solution of ciclosporin in olive oil, whereas U.S. Pat. No. 5,411,952 also describes solutions of ciclosporin in corn oil.

One of the disadvantages of all oil-based formulations for ophthalmic administration is that inherently have a negative impact on vision. Whether used as oily solutions or oil-in-water emulsions, they exhibit a refractive index which differs substantially from that of physiological tear fluid, which leads to visual disturbances and blurring.

Moreover, oil-based formulations do not readily mix with tear fluid to form a homogenous liquid phase. Oily solutions are altogether immiscible with the aqueous tear fluid, and the exact fate of an emulsion mixed with tear fluid in a physiological setting is not completely predictable.

Oil-in-water emulsions of poorly water-soluble drugs like ciclosporin further exhibit the disadvantage that they have a limited drug load capacity. While the active ingredient may have some solubility in the oil phase, this phase is only dispersed in the coherent aqueous phase of the emulsion so that the maximum overall drug concentration in the formulation is very limited.

In contrast to single phase systems such as aqueous or oily solutions, oil-in-water emulsions are also more complex and difficult to manufacture, especially in sterile form. Frequently, emulsions are not readily sterilisable by thermal treatment without negative impact on the physical properties of the emulsion. On the other hand, aseptic processing is complex, costly, and is associated with higher risks of failure, i.e. microbial contamination of the product.

Furthermore, oil-in-water emulsions are like aqueous solutions prone to microbial contamination during use. If they were to be presented in multi-dose containers which are in principle more cost-efficient and convenient for patients than single-use vials, they would have to be preserved in order to ensure their microbiological quality. At the same time, preservatives which can be used in ophthalmic formulations are potentially damaging to the eye, in particular to the ocular surface, and should be avoided in the context of dry eye disease.

WO 2005/123035 discloses hydrophobic compositions which may be useful as ophthalmic drug formulations. The compositions may be used to treat various ophthalmic diseases and conditions including dry eye syndrome and may comprise a therapeutic agent selected from various different therapeutic categories such as antibiotics, antimicrobials, antifungal agents, antiviral agents, antiparasitic agents, anti-allergic agents, anti-inflammatory agents, alkylating agents, beta-blockers, cholinergic agents, vasoconstrictors, pupil size management agents, glaucoma agents, macular degeneration agents, and agents to arrest the development of cataracts. The hydrophobicity of the composition is achieved by selecting a hydrophobic liquid vehicle, selected in particular from silicon polymers, fluorinated silicon polymers, perfluorocarbons, fluorinated alcohols, and perfluorinated polyethers, and mixtures thereof. However, the only specific composition disclosed in the document does not incorporate an active ingredient, but is merely a vehicle consisting of a mixture of two silicon polymers, namely dimethicone and cyclomethicone, which have been combined so as to yield a viscosity of about 8,000 centistokes.

U.S. Pat. No. 6,262,126 discloses semifluorinated alkanes and their preparation, and proposes their use as vehicles in ophthalmic preparations. However, it does not disclose any specific compositions comprising a semifluorinated alkane and an incorporated active ingredient. Neither does it mention the treatment of dry eye syndrome or the incorporation of a macrolide immunosuppressant. It is also silent about ophthalmic vehicles comprising mixtures of semifluorinated alkanes and cosolvents.

It is there an object of the present invention to provide a novel pharmaceutical composition which is useful in the treatment of keratoconjunctivitis sicca, and which at the same time addresses these issues and overcomes at least one of the limitations or disadvantages associated with prior art formulations. In a specific aspect, it is an object of the invention to provide an ophthalmic composition which has the capacity to incorporate substantial amounts of poorly water-soluble drug substances useful in the management of keratoconjunctivitis sicca. In a further aspect, it is an object of the invention to provide a pharmaceutical kit comprising a composition for the treatment of keratoconjunctivitis sicca which does not exhibit one or more of the disadvantages of prior art. Further objects of the invention will become clear on the basis of the following description, examples, and patent claims.

SUMMARY OF THE INVENTION

The present invention provides a pharmaceutical composition comprising an active ingredient useful in the prevention or therapy of keratoconjunctivitis sicca or a symptom associated therewith. The active ingredient is selected from the group of macrolide immunosuppressants. The composition further comprises a liquid vehicle comprising a semifluorinated alkane.

In one of the preferred embodiments, the composition comprises a therapeutically effective amount of a poorly water-soluble macrolide with immunosuppressant activity such as ciclosporin, in particular ciclosporin A. It is furthermore preferred that the composition is in liquid form and adapted to be administered locally into the eye of a patient.

In a further aspect, the invention provides the use of such composition in the prevention or therapy of keratoconjunctivitis sicca or any symptom associated therewith, wherein the prevention or treatment is preferably performed by administering the composition into the eye of a patient.

In yet a further aspect, the invention provides a pharmaceutical kit comprising such composition in a container which has a dispensing means adapted for topically administering the composition to the eye of a patient.

DETAILED DESCRIPTION OF THE INVENTION

In a first aspect, the invention provides a pharmaceutical composition comprising a therapeutically effective amount of an active ingredient useful in the prevention or therapy of keratoconjunctivitis sicca or a symptom associated therewith. The active ingredient is selected from the group of macrolide immunosuppressants. The composition is further characterised in that it comprises a liquid vehicle comprising a semifluorinated alkane.

As used herein, a pharmaceutical composition is a composition comprising at least one pharmacologically active ingredient or diagnostic agent in combination with at least one pharmaceutical excipient. A therapeutically effective amount refers to a dose, concentration or strength which is useful for producing a desired pharmacological effect.

Keratoconjunctivitis sicca is a complex, multifaceted disease or condition as described above. It is also known as dry eye syndrome, dry eye disease (DED), or dysfunctional tear syndrome. Aqueous-deficient DED, evaporative DED, Sjögren syndrome, lacrimal gland insufficiency, meibomian gland disease and other conditions are all within the scope of keratoconjunctivitis sicca and form specific subtypes thereof. Symptoms of keratoconjunctivitis sicca include a dry, scratchy, gritty, or sandy feeling in the eye; foreign body sensation; pain or soreness; stinging or burning; itching;

increased blinking; eye fatigue; photophobia; blurry vision; redness; mucus discharge; contact lens intolerance; excessive reflex tearing. It is understood that not all patients suffering from keratoconjunctivitis sicca exhibit all symptoms simultaneously. Hence, there is currently no uniform set of criteria for diagnosing the disease. It is however important to note that, within the scope of the present invention, any of the aspects, symptoms or pathophysiological consequences of DED may be addressed.

The active ingredient used in the composition of the invention may thus be an agent known to be effective against the disease itself, such as ciclosporin which is believed to intervene in the inflammatory cascades associated with DED, or it may be an agent effective against one or more of the symptoms associated with it, without curative activity. As will be discussed in more detail below, the active ingredient is selected from macrolide immunosuppressants such as ciclosporin, tacrolimus, pimecrolimus, everolimus, sirolimus, deforolimus, temsirolimus, and zotarolimus, abetimus, gusperimus, and mycophenolic acid.

Some of the key advantages of the present invention are brought about by the presence of a semifluorinated alkane in the composition. Semifluorinated alkanes are linear or branched alkanes some of whose hydrogen atoms have been replaced by fluorine. In a preferred embodiment, the semifluorinated alkanes (SFA's) used in the present invention are composed of at least one non-fluorinated hydrocarbon segment and at least one perfluorinated hydrocarbon segment. Particularly useful are SFA's which have one non-fluorinated hydrocarbon segment attached to one perfluorinated hydrocarbon segment, according to the general formula $F(CF_2)_n(CH_2)_mH$, or two perfluorinated hydrocarbon segments separated by one non-fluorinated hydrocarbon segment, according to the general formula $F(CF_2)_n(CH_2)_m(CF_2)_oF$.

Another nomenclature which is used herein refers to the above-mentioned SFA's having two or three segments as RFRH and RFRHRF, respectively, wherein $R_F$ designates a perfluorated hydrocarbon segment, $R_H$ designates a non-fluorinated segment. Alternatively, the compounds may be referred to as FnHm and FnHmFo, respectively, wherein F means a perfluorated hydrocarbon segment, H means a non-fluorinated segment, and n, m and o is the number of carbon atoms of the respective segment. For example, F3H3 is used for perfluoropropylpropane. Moreover, this type of nomenclature is usually used for compounds having linear segments. Therefore, unless otherwise indicated, it should be assumed that F3H3 means 1-perfluoropropylpropane, rather than 2-perfluoropropylpropane, 1-perfluoroisopropylpropane or 2-perfluoroisopropylpropane.

Preferably, the semifluorinated alkanes according to the general formulas $F(CF_2)_n(CH_2)_mH$ and $F(CF_2)_n(CH_2)_m(CF_2)_oF$ have segment sizes ranging from 3 to 20 carbon atoms, i.e. n, m and o are independently selected in the range from 3 to 20. SFA's which are useful in the context of the present invention are also described in EP-A 965 334, EP-A 965329 and EP-A 2110126, the disclosure of which documents is incorporated herein.

In a further embodiment, the semifluorinated alkane is a compound according to the formula RFRH, whose segments $R_F$ and $R_H$ are linear and each—but independently from one another—have from 3 to 20 carbon atoms. In another particular embodiment, the perfluorinated segment is linear and comprises from 4 to 12 carbon atoms, and/or the non-fluorinated segment is linear and comprises from 4 to 8 carbon atoms. Preferred SFA's include in particular the compounds F4H5, F4H6, F6H4, F6H6, F6H8, and F6H10. Presently most preferred for carrying out the invention are F4H5, F6H6 and F6H8.

Optionally, the composition may comprise more than one SFA. It may be useful to combine SFA's, for example, in order to achieve a particular target property such as a certain density or viscosity. If a mixture of SFA's is used, it is furthermore preferred that the mixture comprises at least one of F4H5, F4H6, F6H4, F6H6, F6H8, and F6H10, and in particular one of F4H5, F6H6 and F6H8. In another embodiment, the mixture comprises at least two members selected from F4H5, F4H6, F6H4, F6H6, F6H8, and F6H10, and in particular at least two members selected from F4H5, F6H6 and F6H8.

Liquid SFA's are chemically and physiologically inert, colourless and stable. Their typical densities range from 1.1 to 1.7 $g/cm^3$, and their surface tension may be as low as 19 mN/m. SFA's of the RFRH type are insoluble in water but also somewhat amphiphilic, with increasing lipophilicity correlating with an increasing size of the non-fluorinated segment.

Liquid SFA's of the RFRH type are being used commercially for unfolding and reapplying a retina, for long-term tamponade as vitreous humor substitute (H. Meinert et al., European journal of Ophthalmology, Vol. 10(3), pp. 189-197, 2000), and as wash-out solutions for residual silicon oil after vitreo-retinal surgery. Experimentally, they have also been used as blood substitutes (H. Meinert et al., Biomaterials, Artificial Cells, and Immobilization Biotechnology, Vol. 21(5), pp. 583-95, 1993). These applications have established SFA's as physiologically well tolerated compounds.

On the other hand, SFA's have not been used as excipients in approved drug products as of today.

It has now surprisingly been found by the inventors that SFA's are particularly suitable as carriers, vehicles or excipients in ophthalmic compositions for topical administration. This is based on the fact that SFA's are capable of dissolving many poorly water-soluble compounds which are of interest in ophthalmology, but also on the discovery that they are unexpectedly well-tolerated by the eye, as shown in preclinical testing. This is very surprising as organic or non-aqueous solvents, perhaps with the exception of oily compounds, are typically very irritating or even highly damaging when administered topically to an eye.

Compared to oily carriers or vehicles in ophthalmic compositions for topical use, SFA's exhibit a refractive index which is much better compatible with the aim of a minimally affected vision: While oily preparation lead to a blurry vision and can therefore not be administered in any situation in which the patient needs a clear vision, SFA's cause little or no blurring.

By illustration, the refractive index of tear fluid is close to that of water, i.e. 1.333 at room temperature (RT). Oils typically have a substantially higher refractive index such as about 1.46 (peanut oil), 1.47 (sesame oil), or 1.48 (castor oil). In contrast, the inventors have determined the refractive indices of various SFA's of interest to be in the region of 1.29 to 1.35, i.e. much closer to that of water. In one of the specific embodiments, the invention is therefore practised with an SFA whose refractive index is from 1.29 to 1.35, and in particular from about 1.30 to about 1.35 at 20° C. The refractive index for selected SFA's is shown in table 1.

TABLE 1

| SFA | Refractive index |
|---|---|
| F4H4 | 1.308 |
| F4H5 | 1.3204 |
| F4H6 | 1.334 |
| F4H7 | 1.3357 |
| F4H8 | 1.348 |
| F6H2 | 1.295 |
| F6H4 | 1.306 |
| F6H6 | 1.3224 |
| F6H7 | 1.3366 |
| F6H8 | 1.3432 |
| F6H9 | 1.3494 |

Moreover, SFA's exhibit a remarkable wetting and spreading behaviour by which they deliver an incorporated active ingredient rapidly and effectively to the corneal surface and conjunctiva. Wetting means the ability of a liquid to establish and maintain contact with a solid surface, resulting from intermolecular interactions when the two are brought together. The balance between adhesive and cohesive forces determines the degree of wetting. The higher the adhesive forces compared to the cohesive forces, the more a drop of liquid will spread across the surface of the solid material. Conversely, very high cohesive forces within the liquid will cause the drop to form a sphere, thus avoiding contact with the surface. Similarly, spreading may also occur at the interface of two liquids which are brought into contact with each ether.

A measure for wetting and spreading is the contact angle θ. The contact angle is the angle at which the liquid-vapour interface meets the solid-liquid or liquid-liquid interface. The tendency of a drop to spread out increases as the contact angle decreases. Thus, the contact angle provides an inverse measure of wettability.

A low contact angle of less than 90° indicates high wettability and/or spreading, whereas a higher contact angle indicates poor wettability and spreading. Perfect wetting and spreading results in a contact angle of 0°, also reported as no measurable contact angle.

The inventors have found that the SFA's used in the present invention, in particular the preferred SFA's, exhibit an excellent wetting of various surfaces which are not easily wetted by conventional drug formulations. For example, the contact angle of both F4H5 and F6H8 on tablets compressed from either trospium chloride or fenofibrate (150 mg of drug substance compressed at 15-20 kN to tablets of 13 mm in diameter) was not measurable, i.e. perfect wetting occurred. It is noted that fenofibrate is an example of a hydrophobic, poorly water-soluble compound, whereas trospium chloride is hydrophilic and water-soluble. In comparison, the contact angle of purified water on the fenofibrate tablet was determined as 92.5°, i.e. the tablet was poorly wetted by water.

A further surprising advantage of SFA's found by the inventors is that they appear to form very small droplets when dispensed from a dropper such as an eye dropper. Without wishing to be bound by theory, it is believed that the small droplet size is a result of an interplay of the SFA's unique properties in terms of their density, viscosity, and surface tension. In any case, it is believed that for topical administration into an eye a small drop or volume of administration is highly advantageous as the capability of the lacrimal sac to accept and hold fluid is extremely limited. In fact, it is very common that the administration of a conventional eye drop formulation based on water or oil immediately leads to a discharge of a substantial fraction of the administered medicine as well as some tear fluid. At the same time, there is a risk that some of the administered dose will be taken up systemically via the nasolacrimal duct. Hence, if an effective dose of an active ingredient can be incorporated in a small volume of liquid which can be dispensed as a very small droplet, this should lead to a substantially increased dosing reliability and reproducibility, thus enhancing the safety and effectiveness of the therapy.

A yet further advantage of the invention which is based on the use of SFA's is that they can be designed or mixed for an optimally adjusted evaporation behaviour after administration. Thus it is possible to formulate an ophthalmic composition which delivers an active compound efficiently to the eye in such a way that the liquid vehicles is subsequently eliminated via evaporation. This is in sharp contrast to oily eye drop vehicles which do not evaporate and thus form non-physiological residues at the site of administration, e.g. in the lacrimal sac.

Moreover, the invention provides a means of formulating non-aqueous ophthalmic compositions which are microbiologically stable. This is due to the fact that SFA's are not normally prone to microbial contamination. Hence, it is possible to formulate preservative-free ophthalmic compositions which are better tolerable for many patients, in particular patients suffering from keratoconjunctivitis sicca.

As mentioned, the active ingredient to be selected for carrying out the invention is a macrolide immunosuppressant useful in the management, prevention or therapy of keratoconjunctivitis sicca or dry eye disease, or of any symptom associated with this disease.

It is believed that the invention is particularly useful if the active compound is selected from poorly water-soluble drug substances which are otherwise challenging to formulate for ophthalmic use. As used herein, a compound is poorly water-soluble if it exhibits a solubility falling into the definitions of "sparingly soluble", "slightly soluble", "very slightly soluble", or "practically insoluble" (according to Ph. Eur. 6th Ed.). Particularly preferred are active ingredients which are "very slightly soluble" or "practically insoluble". In another embodiment, it is preferred that the active ingredient exhibits a water solubility of less than about 1 mg per mL, as measured at room temperature (between 15 and 25° C.) and at neutral pH (pH 6.0 and pH 8.0).

An example of a particularly preferred active ingredient is ciclosporin A, which has been discussed in more detail above. Ciclosporin is practically insoluble in water. Ciclosporin may be incorporated at any therapeutically useful concentration, such as from about 0.001 wt.-% to about 5 wt.-%. In a further embodiment, the concentration of ciclosporin is at least about 0.01 wt.-%, such as from about 0.01 wt.-% to about 2 wt.-%, or from about 0.01 wt.-% to about 1 wt.-%, or from about 0.01 wt-% to about 0.5 wt.-%, respectively. Therapeutically useful concentrations of ciclosporin also include 0.02 wt.-%, 0.05 wt.-%, 0.1 wt.-%, and 0.2 wt.-%.

It is also preferred that the active ingredient is incorporated in the dissolved state. This allows the composition to be formulated as a clear solution. Alternatively, the composition may also be designed as a suspension or emulsion.

It has been found by the inventors that certain SFA's have a surprisingly high capacity to dissolve even extremely challenging poorly soluble compounds such as ciclosporin A. In some of the preferred embodiments, ophthalmic solutions comprise an SFA selected from F4H5, F4H6, F6H6, and F6H8 and ciclosporin A as active ingredient. Within these embodiments, it is preferred that the concentration of ciclosporin A is about 0.01 wt.-% to about 0.5 wt.-%.

Depending on the active ingredient, its dose and the SFA or mixture of SFA's selected as carrier, it may be useful to add another liquid excipient in order to ensure that the active compound can be incorporated in completely dissolved form. Such other liquid excipient is preferably an organic cosolvent, such as an oil selected from glyceride oils, liquid waxes, and liquid paraffin, or an organic solvent exhibiting a high degree of biocompatibility.

Examples of potentially useful oily excipients which may be used in combination with one or more SFA's include triglyceride oils (i.e. soybean oil, olive oil, sesame oil, cotton seed oil, castor oil, sweet almond oil), mineral oil (i.e. petrolatum and liquid paraffin), medium chain triglycerides (MCT), oily fatty acids, isopropyl myristate, oily fatty alcohols, esters of sorbitol and fatty acids, oily sucrose esters, or any other oily substance which is physiologically tolerated by the eye.

Examples of potentially useful organic solvents include glycerol, propylene glycol, polyethylene glycol, and ethanol. However, the concentration of the cosolvent should preferably be low relative to that of the SFA or SFA mixture. If an organic solvent such as ethanol is used, it is recommendable to keep it below a level of approx 5 wt.-%. More preferably, the content of ethanol is from about 0.1 to about 2 wt.-%, and most preferably not more than about 1 wt.-%. In one of the specific embodiments, a solution of ciclosporin (e.g. having a concentration of 0.5 mg/mL) in a liquid vehicle comprising about 99 wt.-% of F4H5 and about 1 wt.-% of ethanol is provided.

While ethanol, generally speaking, is not very well tolerated by the human eye, it has surprisingly been found by the inventors that mixtures of semifluorinated alkanes with very small amounts of ethanol, such as 1 wt.-%, are capable of dissolving substantially higher amounts of a hydrophobic, poorly soluble compound such as ciclosporin A, whereas the tolerability of the composition is not negatively affected by the ethanol content.

The composition may of course comprise further pharmaceutical excipients as required or useful. Potentially useful excipients include surfactants, in particular non-ionic surfactants or amphiphilic lipids, acids, bases, antioxidants, stabilisers, synergists, and—if required in a particular case—a preservative.

Surfactants which are considered potentially useful include tyloxapol, poloxamers such as Pluronic F68LF or Lutrol F68, Pluronic L-G2LF and Pluronic L62D, polysorbates such as polysorbate 20 and polysorbate 80, polyoxyethylene castor oil derivatives, sorbitan esters, polyoxyl stearates, and mixtures of two or more thereof.

Furthermore, the invention provides a pharmaceutical kit comprising the composition as described above and a container holding the composition. Preferably, the container which contains the composition has a dispensing means such as a dropping device adapted for topically administering the composition to the eye of a patient.

The following examples serve to illustrate the invention; however, these are not to be understood as restricting the scope of the invention.

EXAMPLES

Example 1

The droplet size of selected SFA's in terms of weight and volume of droplets from three droppers was determined and compared to that of purified water. The devices used for dispensing the droplets were (a) a 2 mL Pasteur pipette (wall thickness 0.53 mm; external tip diameter: 1.50 mm; length: 150 mm) made of glass, (b) a 20 G (0.9 mm×50 mm) injection needle, and (c) a dropper from a commercial eye drops product (Hylo-Vision). The droplet weights were measured at 25° C. using a laboratory balance; the volumes were calculated. Each test was performed 10 times. The results of the experiments (mean values of droplet sizes and standard deviations) are shown in table 2.

TABLE 2

|          | Glass pipette | | Injection needle | | Eye dropper | |
|----------|---------------|-----|------------------|-----|-------------|-----|
| Material | mg | µL | mg | µL | mg | µL |
| Water | 31.2 ± 1.4 | 31.3 ± 1.4 | 11.0 ± 0.9 | 11.1 ± 0.9 | 36.0 ± 2.2 | 36.1 ± 2.2 |
| F4H5  | 6.0 ± 0.4  | 4.7 ± 0.3  | 2.6 ± 0.4  | 2.0 ± 0.3  | 12.4 ± 0.2 | 9.6 ± 0.2  |
| F6H8  | 6.6 ± 0.6  | 5.0 ± 0.4  | 3.4 ± 0.2  | 2.5 ± 0.1  | 13.7 ± 0.4 | 10.3 ± 0.3 |

Table 2 shows that droplets of F4H5 and F6H8 are dramatically smaller and lighter than water droplets dispensed from the same device. Taking into account the fact that SFA's have a high capacity to dissolve many active ingredients very well, it is concluded that SFA's are highly suitable liquid vehicles for eye drops which are better retained by the lacrimal sac, produce little spill-over, and thus have a potential to deliver a dose more reliably and reproducibly to the eye than conventional eye drop formulations.

Example 2

The solubility of ciclosporin A in various semifluorinated alkanes and was tested according to Ph. Eur. 2.2.29, using a reversed-phase HPLC/DAD method. The results are given in table 3.

TABLE 3

| SFA | Solubility [g/L] |
|-----|------------------|
| F4H5 | 2.54 |
| F4H6 | 3.60 |
| F6H6 | 3.61 |
| F6H8 | 1.56 |

Example 3

In the same manner as in example 2, the solubility of ciclosporin A in mixtures of an SFA with 1.0 wt.-% ethanol (EtOH) was determined. The results are given in table 4. They indicate that even a small amount of ethanol, such as 1 wt.-%, increases the solubility of semifluorinated alkanes markedly, and that this effect is particularly pronounced with F4H5.

TABLE 4

| Solvent | Solubility [g/L] | Effect of EtOH |
|---------|------------------|----------------|
| F4H5/EtOH | 5.65 | +122% |
| F6H8/EtOH | 1.77 | +13%  |

Example 4

Ethanol was mixed with F4H5 to yield a solution having an ethanol concentration of 1 wt.-%. 2.5 mg of ciclosporin A were dissolved in 5 ml of this solution, resulting in a clear solution having a ciclosporin concentration of 0.5 mg/mL. The solution was filtered aseptically and filled into sterile vials. The refractive index at 20° C. was 1.321.

Example 5

A solution of ciclosporin A in a mixture of F4H5 and 1 wt.-% ethanol having a nominal ciclosporin concentration of 0.5 mg/mL (as in Example 4) was filled into sterile glass vials (10 mL) and stored at 25° C. and 60% relative humidity. Samples were drawn at the beginning of the storage period and at certain time intervals thereafter, and the concentration of ciclosporin A was determined according to Ph. Eur. 2.2.29, using a reversed-phase HPLC/DAD method. The results are given in table 5.

TABLE 5

| Time | Conc. [g/L] | Assay [%] |
|---|---|---|
| Initial | 0.522 | 104.4 |
| 2 months | 0.522 | 104.4 |
| 3 months | 0.522 | 104.3 |

Example 6

The physiological tolerability of F4H5 and of the vehicle used in example 4 (1 wt.-% ethanol in F4H5) was evaluated in an ex-vivo eye irritation test (EVEIT) using rabbit eyes taken from freshly sacrificed animals. The eyes were fastened in chambers coupled micropump systems which continuously supplied the eyes with cultivation medium (Minimal Essential Medium, MEM T031-05) without fetal calf serum. The vitality of the eyes was monitored by regularly measuring the concentration of lactate and glucose in the chamber eluate. The corneal surface of the eyes was damaged by abrasion, using a dental ceramic abrasive (638XF, Meisinger). For each eye, four lesions of 3.0 to 4.5 mm² were prepared.

To evaluate the effect of F4H5 and F4H5 with 1 wt.-% ethanol on the cornea, an amount of approx. 0.25 to 0.50 μl of the respective test substance was dropped onto the centre of a cornea once every hour over a period of 12 hours, followed by a 12 hour resting period in which the cornea was submersed in culture medium to simulate a closed lid during a night phase. In addition, an aqueous solution of hyaluronic acid (0.1 wt.-%) was used as reference (hyaluronic acid is know to enhance the restoration of the corneal surface after damage), culture medium was used as control, and aqueous benzalkonium chloride solution (0.01 wt.-%) was used as negative control.

Each test was performed over a period of 3 days. The effects were observed by optical coherence tomography (OCT), by digitally determining the dimensions of the lesions after staining with fluorescein, and finally by a histological evaluation of the corneal epithelium and endothelium at the end of each experiment.

In result, it was found that in particular F4H5 was better tolerated than culture medium, and that it exhibits a positive effect on the healing of damaged cornea similar to that of hyaluronic acid. Even when comprising 1 wt.-% of ethanol, F4H5 is tolerated very well by the eye, OCT imaging revealed no indication of penetration of F4H5 into the cornea.

TABLE 6

|  | F4H5 | | | F4H5 + 1% EtOH* | |
|---|---|---|---|---|---|
|  | Run 1 | Run 2 | Run 3 | Run 1 | Run 2 |
| Initial size [mm²] | 9.95 | 12.88 | 12.09 | 14.68 | 14.99 |
| Final size [mm²] | 0.19 | 1.01 | 0.06 | 0.30 | 2.26 |
| Change [%] | −98.1 | −99.0 | −99.5 | −98.0 | −84.9 |

*EtOH: ethanol

TABLE 7

|  | HA | | | MEM | | | |
|---|---|---|---|---|---|---|---|
|  | Run 1 | Run 2 | Run 3 | Run 1 | Run 2 | Run 3 | BAC |
| Initial size [mm²] | 13.22 | 16.03 | 14.87 | 15.5 | 15.57 | 13.11 | 16.05 |
| Final size [mm²] | 0.36 | 0.24 | 0.00 | 2.51 | 6.83 | 0.00 | >60 |
| Change [%] | −97.3 | −98.5 | −100 | −83.8 | −56.1 | −100 | ** |

*HA: hyaluronic acid; BAC: benzalkonium; MEM: minimal essential medium
**Lesion essentially covered the complete corneal surface In more detail, it was found that the lesions prepared by abrasion became smaller or larger over time depending on the liquid that was administered to the cornea. Substantial healing occurred when F4H5, F4H5 with 1 wt-% ethanol, or hyaluronic acid was used. In marked contrast, benzalkonium chloride administration lead to a rapid growth of the lesions eventually leading to a complete disintegration of the corneal epithelium. Culture medium had an intermediate effect. Tables 6 and 7 shows the dimensions of the lesions [mm²] before and after the tests with the various test liquids and controls, respectively.

Morphological and histological evaluation revealed that the corneas treated with F4H5 or hyaluronic acid had not only healed very well, but were also entirely clear at the end of the tests, with healthy and smooth surface morphology. Eyes treated with F4H5 with 1 wt-% ethanol showed a healthy overall morphology, the corneas were clear and the epithelia revealed only very minor signs of damage remaining from the lesions. In contrast, some of the controls treated with culture medium showed significant surface roughness, and the eye treated with benzalkonium chloride showed not only the complete disintegration of the corneal epithelium, but also a major impairment of the complete cornea even including the endothelium.

Example 7

The ex-vivo eye irritation test (EVEIT) according to example 6 was repeated, this time using F6H8 and F6H8 mixed with 1 wt-% ethanol as vehicles whose tolerability was to be evaluated. Each of the two vehicles was tested in two separate runs. In result, all lesions healed fully during the experimental time (see table 8). Histology showed dense stromata with very few clefts and well-arranged keratocytes.

TABLE 8

|  | F6H8 | | F6H8 + 1% EtOH | |
| --- | --- | --- | --- | --- |
|  | Run 1 | Run 2 | Run 1 | Run 2 |
| Initial size [mm$^2$] | 10.54 | 12.08 | 16.65 | 11.29 |
| Final size [mm$^2$] | 0.00 | 0.00 | 0.00 | 0.00 |
| Change [%] | −100.0 | −100.0 | −100.0 | −100.0 |

Example 8

2.5 mg of ciclosporin A were dissolved in 5 ml of a solution of ethanol (1 wt.-%) in F6H8. The resulting clear solution was aseptically filtered and filled into sterile vials. The refractive index at 20° C. was 1.3440.

Example 9

2.5 mg of ciclosporin A and 20 mg of α-tocopherol were dissolved in 5 ml of a solution of ethanol (1 wt.-%) in F4H5. The resulting clear and slightly yellow solution was aseptically filtered and filled into sterile vials. The refractive index at 20° C. was 1.3225.

Example 10

2.5 mg of ciclosporin A were dissolved in 5 mL of a liquid vehicle consisting of F4H5 (49.5 wt.-%), F6H8 (49.5 wt.-%), and ethanol (1 wt.-%). A clear solution resulted, which was aseptically filtered and filled into sterile vials. The refractive index at 20° C. was 1.3310.

Example 11

2.5 mg of ciclosporin A and 20 mg of olive oil were dissolved in 5 mL of a liquid vehicle consisting of F4H5 (49.5 wt.-%), F6H8 (49.5 wt-%), and ethanol (1 wt.-%). A clear and slightly yellow solution resulted, which was aseptically filtered and filled into sterile vials. The refractive index at 20° C. was 1.3431.

Example 12

2.5 mg of tacrolimus were dissolved in 5 mL of a liquid vehicle consisting of F6H8 (99 wt.-%), and ethanol (1 wt.-%). A clear solution resulted, which was aseptically filtered and filled into sterile vials. The refractive index at 20° C. was 1.3421.

Example 13

2.5 mg of tacrolimus were dissolved in 5 mL of a liquid vehicle consisting of F4H5 (99 wt.-%), and ethanol (1 wt.-%). A clear solution resulted, which was aseptically filtered and filled into sterile vials. The refractive index at 20° C. was 1.3218.

The invention claimed is:

1. A pharmaceutical composition comprising:
   (a) a therapeutically effective amount of an active ingredient selected from the group of macrolide immunosuppressants useful in the prevention or therapy of keratoconjunctivitis sicca or a symptom associated therewith, and
   (b) liquid vehicle comprising a semifluorinated alkane, wherein the pharmaceutical composition is formulated as a clear solution.

2. The composition of claim 1, wherein the active ingredient exhibits a water solubility of less than about 1 mg per ml, as measured at room temperature and neutral pH.

3. The composition of claim 2, wherein the active ingredient is ciclosporin A.

4. The composition of claim 3, wherein the concentration of ciclosporin A is from about 0.01 wt.-% to about 0.5 wt.-%.

5. The composition of claim 1, wherein the semifluorinated alkane is a compound of formula
   RFRH
or of formula
   RFRHRF
wherein RF is a perfluorinated hydrocarbon segment with 20 or less carbon atoms, and
wherein RH is a non-fluorinated hydrocarbon segment with 3 to 20 carbon atoms.

6. The composition of claim 5, wherein the semifluorinated alkane is a compound of formula
   RFRH
wherein RF is a linear perfluorinated hydrocarbon segment with 3 to 10 carbon atoms, and
wherein RH is a linear alkyl group with 3 to 10 carbon atoms.

7. The composition of claim 6, wherein the semifluorinated alkane is selected from F4H5, F4H6, F6H6 and F6H8.

8. The composition of claim 1, being effectively free of water.

9. The composition of claim 1, further comprising an organic cosolvent.

10. A pharmaceutical composition comprising:
    (a) a therapeutically effective amount of an active ingredient selected from the group of macrolide immunosuppressants useful in the prevention or therapy of keratoconjunctivitis sicca or a symptom associated therewith;
    (b) a liquid vehicle comprising a semifluorinated alkane; and
    (C) ethanol.

11. The composition of claim 10, comprising ethanol at a concentration of about 1 wt.-% or less.

12. A pharmaceutical kit comprising the composition of claim 1 and a container holding the composition, wherein the container has a dispensing means adapted for topically administering the composition to the eye of a patient.

13. The composition of claim 6, wherein the semifluorinated alkane is F4H5.

* * * * *